(12) United States Patent
Jolidon et al.

(10) Patent No.: US 6,951,884 B2
(45) Date of Patent: Oct. 4, 2005

(54) FLUOROBENZAMIDES AND USES THEREOF

(75) Inventors: Synese Jolidon, Blauen (CH); Rosa Maria Rodriguez Sarmiento, Basel (CH); Andrew William Thomas, Birsfelden (CH); Rene Wyler, Zurich (CH)

(73) Assignee: Hoffmann-La Roche Inc., Nutley, NJ (US)

(*) Notice: Subject to any disclaimer, the term of this patent is extended or adjusted under 35 U.S.C. 154(b) by 123 days.

(21) Appl. No.: 10/456,641

(22) Filed: Jun. 6, 2003

(65) Prior Publication Data

US 2003/0236304 A1 Dec. 25, 2003

(30) Foreign Application Priority Data

Jun. 12, 2002 (EP) .............................. 02012484

(51) Int. Cl.[7] ...................... A61K 31/275; A61K 31/16; C07C 255/55; C07C 233/65
(52) U.S. Cl. ...................... 514/522; 514/616; 514/622; 558/392; 558/415; 564/155; 564/171
(58) Field of Search ................ 564/155, 171; 558/392, 415; 514/616, 622

(56) References Cited

U.S. PATENT DOCUMENTS

| | | |
|---|---|---|
| 4,906,626 A | 3/1990 | Amrein et al. |
| 5,889,026 A * | 3/1999 | Alanine et al. ............. 514/326 |

FOREIGN PATENT DOCUMENTS

EP    0 326 023    8/1989

OTHER PUBLICATIONS

Bach et al., Proc. Natl. Acad. Sci. USA, 85 pp. 4934–4938 (1988).
Cesura et al., Prog. Drug Research, 38, 171–297 (1992).
Fowler et al., J. Neural. Tranm., 49, pp. 1–20 (1980).
Benedetti et al., Biochem. Pharmacol., 38, pp. 555–561 (1989).
Saura et al., Neuroscience, 70, 755–774 (1996).
Bentué–Ferrer et al., CNS Drugs, 6, pp. 217–236 (1996).
Zhou et al., Analytical Biochemistry, 253, pp. 169–174 (1997).

* cited by examiner

Primary Examiner—Johann Richter
Assistant Examiner—Ebenezer Sackey
(74) Attorney, Agent, or Firm—George W. Johnston; Patricia S. Rocha-Tramaloni; Kimberly J. Prior

(57) ABSTRACT

The invention relates to fluorobenzamide derivatives of the formula

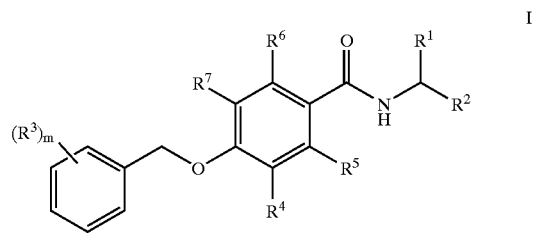

wherein $R^1$, $R^2$, $R^3$ $R^4$, $R^5$, $R^6$ and $R^7$ are as defined herein. =, The compounds of the invention are selective monoamine oxidase B inhibitors and therefore they are suitable for the treatment of diseases mediated by monoamine oxidase B, such as Alzheimer's disease or senile dementia.

45 Claims, No Drawings

FLUOROBENZAMIDES AND USES THEREOF

FIELD OF THE INVENTION

The present invention relates to new fluorobenzamide derivatives, to processes and intermediates for their preparation, and to pharmaceutical compositions containing them. These compounds are selective monoamine oxidase inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, Prog. Drug Research 1992, 38, 171–297). Brain MAO-B activity appears to increase with age. This increase has been attributed to the gliosis associated with aging (C. J. Fowler et al., *J. Neutral. Transm.* 1980, 49, 1–20). Additionally, MAO-B activity is significantly higher in the brains of patients with Alzheimer's disease (P. Dostert et al., *Biochem. Pharmacol.* 1989, 38, 555–561) and it has been found to be highly expressed in astrocytes around senile plaques (Saura et al., *Neuroscience* 1994, 70, 755–774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

It is an object of the present invention to provide compounds having the following formula

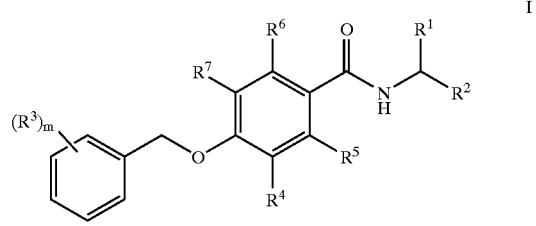

in which $R^1$, $R^2$, $R^3$, $R^4$, $R^5$, $R^6$, and $R^7$, are as defined herein. The invention also provides for pharmaceutically acceptable salts of these compounds.

It has been found that the compounds of the present invention are highly selective MAO-B inhibitors. Therefore, it is another object of the invention to provide compositions containing one or more compounds of formula I and a pharmaceutically acceptable carrier. It is a further object of the invention to provide methods for the treatment of prevention of diseases mediated by monoamine oxidase B. It is also an object of the present invention to provide a process for the manufacture of compounds of the invention, for example, compounds of formula I.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$C_1$–$C_6$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine.

"Halogen-($C_1$–$C_6$)-alkyl" or "halogen-($C_1$–$C_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogenalkoxy" includes trifluoromethyloxy.

"$C_1$–$C_6$-Alkoxy" means the residue —O—R, wherein R is a lower alkyl residue as defined herein. Examples of alkoxy radicals include, but are not limited to, methoxy, ethoxy, isopropoxy, and the like.

"Hydroxy-($C_1$–$C_6$)-alkyl" means the lower alkyl residue as defined herein substituted in any position with one or more hydroxyl groups as. An example of a hydroxyalkyl residue is the hydroxymethyl group.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

It is an object of the present invention to provide compounds having the following formula

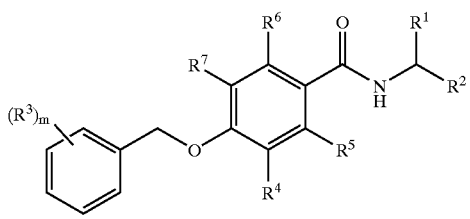

wherein
$R^1$ is hydrogen, $(C_1-C_6)$-alkyl or hydroxy-$(C_1-C_6)$-alkyl;
$R^2$ is $(C_1-C_6)$-alkyl,
  —CO—$NR^8R^9$,
  —$(CH_2)_n$—$NR^8R^9$,
  —$(CH_2)_p$—$OR^8$, or
  —$(CH_2)_n$—CN;
$R^3$ is selected from hydrogen, halogen, halogen-$(C_1-C_6)$-alkyl, cyano, $(C_1-C_6)$-alkoxy, or halogen-$(C_1-C_6)$-alkoxy;
$R^4$, $R^5$, $R^6$ and $R^7$ are hydrogen or fluoro, wherein at least one of $R^4$, $R^5$, $R^6$ and $R^7$ is fluoro;
$R^8$ and $R^9$ are each independently hydrogen or $(C_1-C_6)$-alkyl;
m is 1, 2, or 3;
n is 0, 1, 2, or 3; and
p is 1 or 2;
or a pharmaceutically acceptable salt thereof.

Among compounds of the present invention certain compounds of formula I, or pharmaceutically acceptable salts thereof, are preferred.

Compounds of formula I are substituted by one, two or three $R^3$ selected from the group consisting of hydrogen, halogen, halogen-$(C_1-C_6)$-alkyl, cyano, $C_1-C_6$-alkoxy or halogen-$(C_1-C_6)$-alkoxy.

Preferably, $R^3$ is selected from the group consisting of halogen, halogen-$(C_1-C_6)$-alkyl, cyano, $C_1-C_6$-alkoxy or halogen-$(C_1-C_6)$-alkoxy. For example, in one embodiment, $R^3$ is preferably $C_1-C_6$-alkoxy, whereas in another embodiment, $R^3$ is preferably cyano. In still another embodiment, $R^3$ is preferably halogen, halogen-$(C_1-C_6)$-alkyl, or halogen-$(C_1-C_6)$-alkoxy.

Preferred compounds of formula I are those, wherein $R^3$ is halogen or halogen-$(C_1-C_6)$-alkyl. Especially preferred are those compounds of formula I, wherein $R^3$ is fluoro or trifluoromethyl. Preferred compounds of formula I are those which are substituted by one $R^3$.

$R^2$ is selected from the following groups: $(C_1-C_6)$-alkyl, —CO—$NR^8R^9$, —$(CH_2)_n$—$NR^8R^9$, —$(CH_2)_p$—$OR^8$, or —$(CH_2)_n$—CN. In one embodiment, preferred compounds of formula I are those in which $R^2$ is —CO—$NR^8R^9$ and $R^8$ and $R^9$ are each independently hydrogen or $(C_1-C_6)$-alkyl. Especially preferred are those compounds of formula I, wherein $R^2$ is —CO—$NH_2$.

In another embodiment, preferred compounds of formula I are those in which $R^2$ is —$(CH_2)_p$—$OR^8$, $R^8$ is hydrogen or $(C_1-C_6)$-alkyl, and p is 1 or 2. Especially preferred are those compounds of formula I, wherein $R^2$ is $CH_2OH$.

In a further embodiment, preferred compounds of formula I are those in which $R^2$ is $(CH_2)_n$—$NR^8R^9$, and $R^8$ and $R^9$ are each independently hydrogen or $(C_1-C_6)$-alkyl, and n is 0, 1, 2, or 3. Especially preferred are those compounds of formula I, wherein $R^2$ is $CH_2NH_2$.

In yet another embodiment, preferred compounds of formula I are those in which $R^2$ is $(CH_2)_n$—CN and n is 0, 1, 2, or 3. Especially preferred are compounds of formula I, wherein $R^2$ is CN or $CH_2CN$.

In a further embodiment, preferred compounds of formula I are those in which $R^2$ is $(C_1-C_6)$-alkyl. For example, preferred compounds include those in which $R^2$ is methyl, ethyl, or propyl. Especially preferred are compounds of formula I, wherein $R^2$ is methyl.

Compounds of formula I are those, wherein $R^4$, $R^5$, $R^6$ and $R^7$ are hydrogen or fluoro and wherein at least one of $R^4$, $R^5$, $R^6$ or $R^7$ is fluoro. Especially preferred are compounds of formula I wherein $R^5$ is fluoro and $R^4$, $R^6$ and $R^7$ are hydrogen.

More preferred are compounds of formula I, wherein $R^5$ is fluoro, $R^4$, $R^6$ and $R^7$ are hydrogen, and wherein $R^2$ is —CO—$NR^8R^9$ and $R^8$ and $R^9$ are each independently hydrogen or $(C_1-C_6)$-alkyl.

Even more preferred are compounds of formula I, wherein $R^5$ is fluoro, $R^4$, $R^6$ and $R^7$ are hydrogen, $R^2$ is —CO—$NR^8R^9$, $R^8$ and $R^9$ are each independently hydrogen or $(C_1-C_6)$-alkyl and wherein $R^3$ is fluoro.

The following are examples of such compounds:
(S)-N-(1-carbamoyl-ethyl)-2-fluoro-4-(3-fluoro-benzyloxy)-benzamide,
2-[4-(3-fluorobenzyloxy)-2-fluoro-benzamido]acetamide,
(S)-N-(1-carbamoyl-2-hydroxy-ethyl)-2-fluoro-4-(3-fluoro-benzyloxy)-benzamide,
(R)-N-(1-carbamoyl-ethyl)-2-fluoro-4-(3-fluoro-benzyloxy)-benzamide,
2-[4-(4-fluorobenzyloxy)-2-fluoro-benzamido]acetamide, and
(S)-N-(1-carbamoyl-ethyl)-2-fluoro-4-(4-fluoro-benzyloxy)-benzamide.

Also preferred are compounds of formula I, wherein $R^5$ is fluoro, $R^4$, $R^6$ and $R^7$ are hydrogen, $R^2$ is —CO—$NR^8R^9$, $R^8$ and $R^9$ are each independently hydrogen or $(C_1-C_6)$-alkyl and wherein $R^3$ is trifluoromethyl.

Examples of such compounds are the following:
(S)-N-(1-carbamoyl-ethyl)-2-fluoro-4-(4-trifluoromethyl-benzyloxy)-benzamide, and
(S)-4-(3,5-bis-trifluoromethyl-benzyloxy)-N-(1-carbamoyl-ethyl)-2-fluoro-benzamide.

A further group of preferred compounds of formula I are those, wherein $R^5$ is fluoro, $R^4$, $R^6$ and $R^7$ are hydrogen, and wherein $R^2$ is —$(CH_2)_p$—$OR^8$, $R^8$ is hydrogen or $(C_1-C_6)$-alkyl and p is 1 or 2.

(S)-2-Fluoro-4-(3-fluoro-benzyloxy)-N-(2-methoxy-1-methyl-ethyl)-benzamide, 2-fluoro-4-(3-fluoro-benzyloxy)-N-(2-methoxy-ethyl)-benzamide and 2-fluoro-4-(3-fluoro-benzyloxy)-N-(2-hydroxy-ethyl)-benzamide are examples therefore.

Another group of preferred compounds of formula I are those, wherein $R^5$ is fluoro, $R^4$, $R^6$ and $R^7$ are hydrogen, and wherein $R^2$ is —$(CH_2)_n$—$NR^8R^9$, $R^8$ and $R^9$ are each independently hydrogen or $(C_1$–$C_6)$-alkyl and n is 0, 1, 2 or 3.

A further group of preferred compounds of formula I are those, wherein $R^5$ is fluoro, $R^4$, $R^6$ and $R^7$ are hydrogen, and wherein $R^2$ is —$(CH_2)_n$—CN and n is 0, 1, 2 or 3.

Yet another group of preferred compounds of formula I are those, wherein $R^5$ is fluoro, $R^4$, $R^6$ and $R^7$ are hydrogen, and wherein $R^2$ is $(CH_2)_p$—$OR^8$, $R^8$ is hydrogen or $(C_1$–$C_6)$-alkyl and p is 1 or 2.

A further group of preferred compounds of formula I are those, wherein $R^5$ is fluoro, $R^4$, $R^6$ and $R^7$ are hydrogen, and wherein $R^2$ is $(CH_2)_n$—CN and n is 0, 1, 2, or 3.

Yet another group of preferred compounds of formula I are those, wherein $R^5$ is fluoro, $R^4$, $R^6$ and $R^7$ are hydrogen, and wherein $R^2$ is $(C_1$–$C_6)$-alkyl.

Also preferred are compounds of formula I, wherein $R^4$ is fluoro and $R^5$, $R^6$ and $R^7$ are hydrogen.

More preferred are compounds of formula I, wherein $R^4$ is fluoro, $R^5$, $R^6$ and $R^7$ are hydrogen, and wherein $R^2$ is —CO—$NR^8R^9$ and $R^8$ and $R^9$ are each independently hydrogen or $(C_1$–$C_6)$-alkyl.

Especially preferred are those compounds of formula I, wherein $R^4$ is fluoro, $R^5$, $R^6$ and $R^7$ are hydrogen, $R^2$ is —CO—$NR^8R^9$ and $R^8$ and $R^9$ are each independently hydrogen or $(C_1$–$C_6)$-alkyl, and wherein $R^3$ is fluoro.

Examples of such compounds are the following:
(S)-N-(1-carbamoyl-ethyl)-3-fluoro-4-(4-fluoro-benzyloxy)-benzamide,
2-[4-(4-fluorobenzyloxy)-3-fluoro-benzamido]acetamide,
(S)-N-(1-carbamoyl-2-hydroxy-ethyl)-3-fluoro-4-(4-fluoro-benzyloxy)-benzamide,
2-[4-(3-fluorobenzyloxy)-3-fluoro-benzamido]acetamide,
(S)-N-(1-carbamoyl-ethyl)-3-fluoro-4-(3-fluoro-benzyloxy)-benzamide,
(R)-N-(1-carbamoyl-ethyl)-3-fluoro-4-(3-fluoro-benzyloxy)-benzamide, and
(S)-N-(1-carbamoyl-2-hydroxy-ethyl)-3-fluoro-4-(3-fluoro-benzyloxy)-benzamide.

Also preferred are compounds of formula I, wherein $R^4$ is fluoro, $R^5$, $R^6$ and $R^7$ are hydrogen, $R^2$ is —CO—$NR^8R^9$ and $R^8$ and $R^9$ are each independently hydrogen or $(C_1$–$C_6)$-alkyl, and wherein $R^3$ is trifluoromethyl.

The following are examples of such compounds:
2-[4-(4-trifluoromethylbenzyloxy)-3-fluoro-benzamido]acetamide, and
(S)-N-(1-carbamoyl-2-hydroxy-ethyl)-3-fluoro-4-(4-trifluoromethyl-benzyloxy)-benzamide.

Further preferred are compounds of formula I, wherein $R^4$ is fluoro, $R^5$, $R^6$ and $R^7$ are hydrogen, and wherein $R^2$ is —$(CH_2)_p$—$OR^8$, $R^8$ is hydrogen or $(C_1$–$C_6)$-alkyl and p is 1 or 2.

Compounds of formula I, wherein $R^4$ is fluoro, $R^5$, $R^6$ and $R^7$ are hydrogen, and wherein $R^2$ is —$(CH_2)_n$—$NR^8R^9$, $R^8$ and $R^9$ are each independently hydrogen or $(C_1$–$C_6)$-alkyl and n is 0, 1, 2 or 3, are also preferred.

Further preferred compounds of formula I are those, wherein $R^4$ is fluoro, $R^5$, $R^6$ and $R^7$ are hydrogen, and wherein $R^2$ is —$(CH_2)_n$—CN and n is 0, 1, 2 or 3.

Additional preferred compounds of formula I are those, wherein $R^4$ is fluoro, $R^5$, $R^6$ and $R^7$ are hydrogen, and wherein $R^2$ is —$(CH_2)_n$—$NR^8R^9$, $R^8$ and $R^9$ are each independently hydrogen or $(C_1$–$C_6)$-alkyl, and n is 0, 1, 2 or 3.

Other preferred compounds of formula I are those, wherein $R^4$ is fluoro, $R^5$, $R^6$ and $R^7$ are hydrogen, and wherein $R^2$ is $(C_1$–$C_6)$-alkyl.

Also preferred are compounds of formula I, wherein $R^6$ is fluoro, $R^4$, $R^5$ and $R^7$ are hydrogen. Other preferred compounds are those wherein $R^7$ is fluoro, $R^4$, $R^5$ and $R^6$ are hydrogen.

In another embodiment, preferred compounds of the invention are compounds of formula I, wherein two of $R^4$, $R^5$, $R^6$, and $R^7$ are fluoro and two of $R^4$, $R^5$, $R^6$, and $R^7$ are hydrogen. For example, such compounds include those wherein $R^4$ and $R^5$ are fluoro and $R^6$ and $R^7$ are hydrogen. Also preferred are compounds wherein $R^4$ and $R^6$ are fluoro and $R^5$ and $R^7$ are hydrogen. Other preferred compounds include those in which $R^4$ and $R^7$ are fluoro and $R^5$ and $R^6$ are hydrogen. Preferred compounds also include those where $R^5$ and $R^6$ are fluoro and $R^4$ and $R^7$ are hydrogen; those where $R^5$ and $R^7$ are fluoro and $R^4$ and $R^6$ are hydrogen; and those where $R^6$ and $R^7$ are fluoro and $R^4$ and $R^5$ are hydrogen.

Also preferred are compounds of formula I, wherein three of $R^4$, $R^5$, $R^6$, and $R^7$ are fluoro and the remaining R group is hydrogen. For example, preferred compounds include those where $R^4$, $R^5$, and $R^6$ are fluoro and $R^7$ is hydrogen; those where $R^4$, $R^6$, and $R^7$ are fluoro and $R^5$ is hydrogen; and those where $R^5$, $R^6$, and $R^7$ are fluoro and $R^4$ is hydrogen. Other preferred compounds are those in which all of $R^4$, $R^5$, $R^6$, and $R^7$ are fluoro.

Furthermore, compounds of formula I, wherein $R^3$ is hydrogen, are also preferred. Compounds of formula I, wherein $R^4$ and $R^5$ are both fluoro and $R^6$ and $R^7$ are hydrogen, are also preferred, for example the following compounds:
(S)-N-(1-carbamoyl-ethyl)-2,6-difluoro-4-(4-fluoro-benzyloxy)-benzamide,
N-carbamoylmethyl-2,6-difluoro-4-(4-fluoro-benzyloxy)-benzamide,
N-cyanomethyl-2,6-difluoro-4-(4-fluoro-benzyloxy)-benzamide,
2,6-difluoro-4-(4-fluoro-benzyloxy)-N-(2-methoxy-ethyl)-benzamide,
(S)-2,6-difluoro-4-(4-fluoro-benzyloxy)-N-(2-hydroxy-1-methyl-ethyl)-benzamide and
2,6-difluoro-4-(3-fluoro-benzyloxy)-N-(2-methoxy-ethyl)-benzamide.

The compounds of formula I and their pharmaceutically acceptable salts can be manufactured by reacting a compound of formula

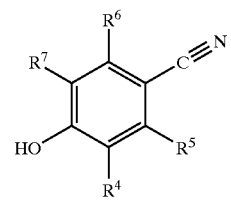

II with a compound of formula

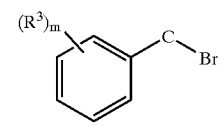

III to obtain a compound of formula

IV

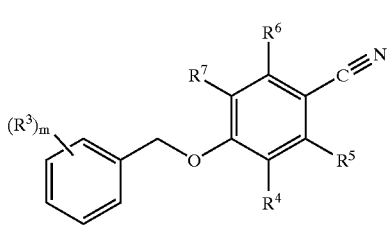

which is transformed to a compound of formula

V

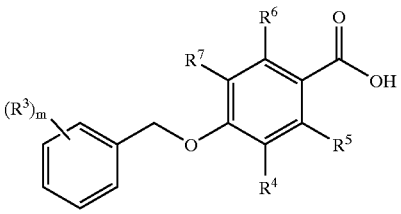

and treated with compounds of formula

VI

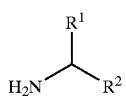

to obtain a compound of formula

I

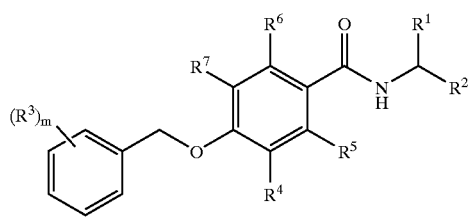

and, if desired, converting a compound of formula I into a pharmaceutically acceptable salt.

In accordance with the present invention, compounds of formula I can be prepared from intermediate compounds V following scheme 3 below. Intermediate compounds of formula V can be prepared, for example, following scheme 1. A compound of formula II is treated with benzylic bromides of formula III in the presence of potassium carbonate to afford compounds of type IV which are then heated with a solution of sodium hydroxide to form the acids of type V.

Scheme 1

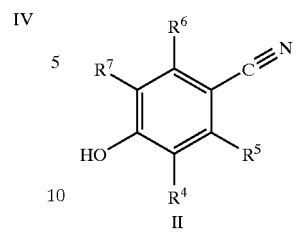

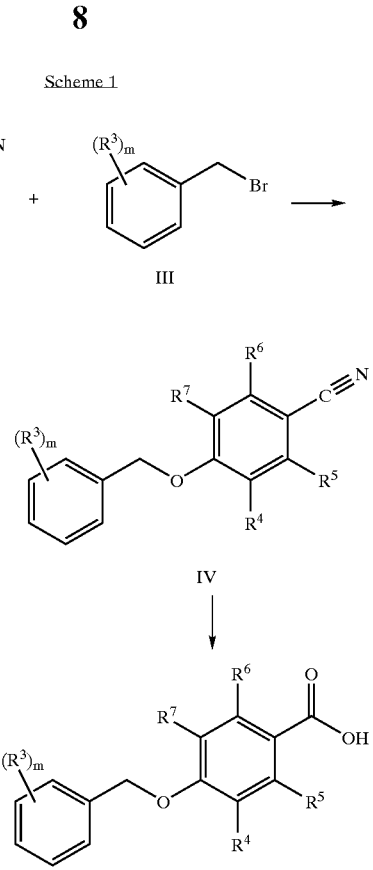

Alternatively the acids V (where $R^5=R^6=F$) can be prepared as shown in Scheme 2, by the O-benzylation of phenols of type IIa to afford IVa which can be ortho metallated (for example lithiated with BuLi), quenched with carbon dioxide and the reaction mixture acidified to afford the acids V.

Scheme 2

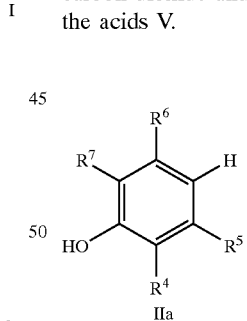

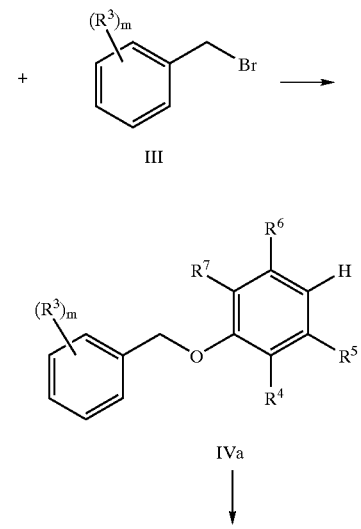

-continued

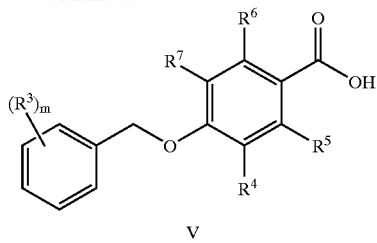

V

Activation of the acids V with carbonyldiimidazole (or other appropriate activating agents) followed by treatment with amines of type VI affords compounds of formula I (scheme 3).

Scheme 3

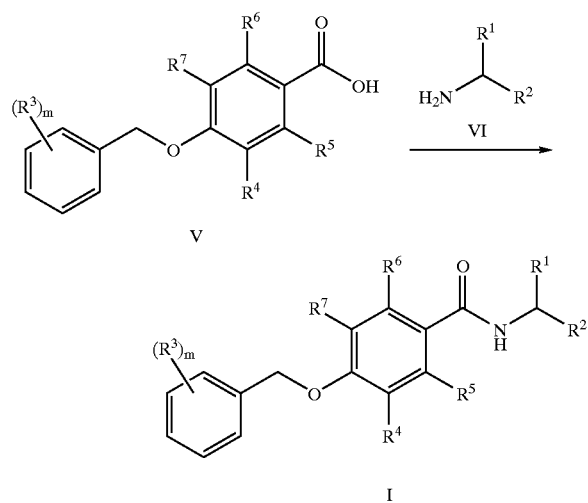

Compounds of Formulae II, IIa, III, and VI are commercially available or can be prepared by methods known to those skilled in the art.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds of formula I.

The compounds of the invention and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The compounds of the invention and their pharmaceutically acceptable salts are especially useful for the treatment and prevention of Alzheimer's disease and senile dementia.

The pharmacological activity of the compounds was tested using the following method:

The cDNA's encoding human MAO-A and MAO-B were transiently transfected into EBNA cells using the procedure described by E.-J. Schlaeger and K. Christensen (Transient Gene Expression in Mammalian Cells Grown in Serum-free Suspension Culture; Cytotechnology, 15: 1–13, 1998). After transfection, cells were homogeneised by means of a Polytron homogeneiser in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by M. Zhou and N. Panchuk-Voloshina (A One-Step Fluorometric Method for the Continuous Measurement of Monoamine Oxidase Activity, Analytical Biochemistry, 253: 169–174, 1997). Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 $\mu$M N-acetyl-3,7,-dihydroxyphenoxazine (Amplex Red, Molecular Probes). The samples were further incubated for 30 min at 37° C. in a final volume of 200 $\mu$l and absorbance was then determined at a wavelength of 570 nm using a SpectraMax plate reader (Molecular Devices). Background (non-specific) absorbance was determined in the presence of 10 $\mu$M clorgyline for MAO-A or 10 $\mu$M L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The activities of compounds of formula I as measured in the assay described above are in the range of 420 nM or less, typically of 100 nM or less, and ideally 30 nM or less. Some data of preferred compounds are described in the table below:

| Example No. | IC$_{50}$, MAO-B inhibition (nM) |
|---|---|
| 1 | 5.9 |
| 2 | 15.3 |
| 4 | 8.0 |
| 5 | 11.6 |
| 6 | 19.5 |
| 10 | 11.6 |
| 11 | 7.0 |
| 12 | 25.7 |
| 18 | 7.0 |
| 19 | 3.1 |
| 20 | 11.0 |
| 22 | 18.0 |
| 25 | 5.0 |
| 26 | 19.0 |
| 27 | 23.0 |
| 28 | 12.0 |
| 31 | 16.0 |
| 34 | 25.0 |
| 36 | 19.0 |
| 37 | 22.0 |
| 39 | 27.0 |
| 41 | 13.0 |
| 45 | 23.0 |
| 51 | 24.0 |

The present invention also provides pharmaceutical compositions containing compounds of the invention or pharmaceutically acceptable salts thereof and a pharmaceutically acceptable carrier. Such pharmaceutical compositions can be in the form tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the present invention are selective MAO-B inhibitors. Therefore, the present invention also provides methods of treating diseases that are mediated by monoamine oxidase B. Such methods include administering a therapeutically effective amount of a compound of the invention, for example, a compound of formula I, or a pharmaceutically acceptable salt thereof, to a patient in need of such treatment. In a preferred embodiment, the invention provides a method for the treatment of Alzheimer's disease. In another preferred embodiment, the present invention provides a method for the treatment of senile dementia.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions or suspensions. The pharmaceutical compositions also can be administered rectally, for example, in the form of suppositories or parenterally, for example, in the form of injection solutions.

The dosage at which the compound of the invention is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof.

EXAMPLE 1

(S)-N-(1-Carbamoyl-ethyl)-2-fluoro-4-(3-fluoro-benzyloxy)-benzamide a) 2-Fluoro-4-(3-fluoro-benzyloxy)-benzonitrile A mixture of 2-fluoro-4-hydroxy-benzonitrile (15.0 g, 109 mmol), 3-fluorobenzyl bromide (22.7 g, 120 mmol) and potassium carbonate (18.1 g, 131 mmol) in dry acetone (250 mL) was heated under reflux for 4 h. After cooling to room temperature the mixture was filtered and the filtrate was evaporated to leave an off-white solid which was washed with hexane to afford the title compound (26.8 g, 100%) as a white solid. MS: m/e=245.2 (M$^+$).

b) 2-Fluoro-4-(3-fluoro-benzyloxy)-benzoic acid

A suspension of 2-fluoro-4-(3-fluoro-benzyloxy)-benzonitrile (24.5 g, 100 mmol) and sodium hydroxide (30 g, 750 mmol) in water (300 mL) was heated under reflux for 16 h. After cooling to room temperature the suspension was acidified to pH 2 with concentrated hydrochloric acid. The resulting mixture was diluted with water (100 mL) and extracted with ether (3×400 mL). The combined organic extracts were then washed with water and brine and then dried over sodium sulfate. Filtration and half evaporation of the filtrate resulted in the formation of a white precipitate which was filtered off to afford the title compound (14 g, 53%) as white crystals after recrystallisation from cyclohexane: ethyl acetate. MS: m/e=263.1 (M–H$^-$)

c) (S)-N-(1-Carbamoyl-ethyl)-2-fluoro-4-(3-fluoro-benzyloxy)-benzamide

A mixture of 2-fluoro-4-(3-fluoro-benzyloxy)-benzoic acid (400 mg, 1.5 mmol) and carbonyldiimidazole (258 mg, 1.6 mmol) in dry THF (5 mL) under Argon was heated under reflux for 30 min. After cooling to room temperature a suspension of H-alanine-NH$_2$ HCl (226 mg, 1.8 mmol) containing triethylamine (184 mg, 1.8 mmol) in dry THF (1 mL) was added and the resulting mixture heated under reflux for 1 h. After cooling to room temperature water (5 mL) was added and the resulting precipitate was filtered off and washed successively with hexane and diethylether to afford the title compound (272 mg, 54%) as a white solid. MS: m/e=335.3 (M+H$^+$).

EXAMPLE 2

2-[4-(3-Fluorobenzyloxy)-2-fluoro-benzamido]acetamide

As described for example 1c, 2-fluoro-4-(3-fluoro-benzyloxy)-benzoic acid (400 mg, 1.5 mmol) was converted to the title compound (375 mg, 77%) (using glycinamide HCl instead of H-alanine-$NH_2$ HCl) which was obtained as a white solid. MS: m/e=321.3 (M−H).

EXAMPLE 3

N-Cyanomethyl-2-fluoro-4-(3-fluoro-benzyloxy)-benzamide

As described for example 1c, 2-fluoro-4-(3-fluoro-benzyloxy)-benzoic acid (400 mg, 1.5 mmol) was converted to the title compound (362 mg, 77%) (using aminoacetonitrile instead of H-alanine-$NH_2$ HCl) which was obtained as a light brown solid. MS: m/e=303.3 ($M+H^+$).

EXAMPLE 4

(S)-2-Fluoro-4-(3-fluoro-benzyloxy)-N-(2-methoxy-1-methyl-ethyl)-benzamide

As described for example 1c, 2-fluoro-4-(3-fluoro-benzyloxy)-benzoic acid (400 mg, 1.5 mmol) was converted to the title compound (471 mg, 93%) [using (S)-1-methoxy-2-propylamine instead of H-alanine-$NH_2$ HCl] which was obtained as a light yellow solid after extraction with ethyl acetate. MS: m/e=336.3 ($M+H^+$).

EXAMPLE 5

(S)-N-(1-Carbamoyl-2-hydroxy-ethyl)-2-fluoro-4-(3-fluoro-benzyloxy)-benzamide

As described for example 1c, 2-fluoro-4-(3-fluoro-benzyloxy)-benzoic acid (400 mg, 1.5 mmol) was converted to the title compound (111 mg, 21%) (using H-serine-$NH_2$ HCl instead of H-alanine-$NH_2$ HCl) which was obtained as a white solid after purification by chromatography (SiO2, ethyl acetate:hexane 1:1). MS: m/e=351.3 ($M+H^+$).

EXAMPLE 6

2-Fluoro-4-(3-fluoro-benzyloxy)-N-(2-methoxy-ethyl)-benzamide

As described for example 1c, 2-fluoro-4-(3-fluoro-benzyloxy)-benzoic acid (400 mg, 1.5 mmol) was converted to the title compound (397 mg, 82%) (using 2-methoxy ethylamine instead of H-alanine-$NH_2$ HCl) which was obtained as a light yellow solid. MS: m/e=322.2 ($M+H^+$).

EXAMPLE 7

N-(2-Amino-ethyl)-2-fluoro-4-(3-fluoro-benzyloxy)-benzamide 1:1 hydrochloride a) 2-[2-Fluoro-4-(3-fluoro-benzyloxy)-benzoylamino]-ethyl}-carbamic acid tert-Butyl ester As described for example 1c, 2-fluoro-4-(3-fluoro-benzyloxy)-benzoic acid (400 mg, 1.5 mmol) was converted to the title compound (546 mg, 89%) [using tert-butyl N-(2-aminoethyl)-carbamate instead of H-alanine-$NH_2$ HCl] which was obtained as a white solid. MS: m/e=407.4 ($M+H^+$).

b) N-(2-Amino-ethyl)-2-fluoro-4-(3-fluoro-benzyloxy)-benzamide 1:1 hydrochloride A mixture of 2-[2-fluoro-4-(3-fluoro-benzyloxy)-benzoylamino]-ethyl}-carbamic acid tert-butyl ester (530 mg, 1.3 mmol) and HCl in dioxane (4 N, 5 mL) was stirred at room temperature for 16 h. The resulting precipitate was filtered off to afford the title compound (400 mg, 90%) which was obtained as a white solid. MS: m/e=341.5 ($M-H^-$).

EXAMPLE 8

2-Fluoro-4-(3-fluoro-benzyloxy)-N-(2-hydroxy-ethyl)-benzamide

As described for example 1c, 2-fluoro-4-(3-fluoro-benzyloxy)-benzoic acid (400 mg, 1.5 mmol) was converted to the title compound (393 mg, 84%) [using ethanolamine instead of H-alanine-$NH_2$ HCl] which was obtained as a white solid. MS: m/e=308.1 ($M+H^+$).

EXAMPLE 9

(R)-N-(1-Carbamoyl-ethyl)-2-fluoro-4-(3-fluoro-benzyloxy)-benzamide

A mixture of 2-fluoro-4-(3-fluoro-benzyloxy)-benzoic acid (1.0 g, 3.8 mmol) and carbonyldiimidazole (675 mg, 4.2 mmol) in dry DMF (10 mL) under Argon was heated under reflux for 30 min. After cooling to room temperature a suspension of H-D-alanine-$NH_2$ HCl (707 mg, 5.7 mmol) containing pyridine (0.49 mL, 6.1 mmol) in dry DMF (5 mL) was added. After 48 h, water (15 mL) was added and the resulting precipitate was filtered off and washed with water to afford the title compound (1.27 g, 100%) as a white solid. MS: m/e=335.3 ($M+H^+$).

EXAMPLE 10

2-[4-(4-Fluorobenzyloxy)-2-fluoro-benzamido]acetamide a) 2-Fluoro-4-(4-fluoro-benzyloxy)-benzonitrile As described for example 1a, 2-fluoro-4-hydroxy-benzonitrile (5.0 g, 36 mmol) [using 4-fluorobenzyl bromide instead of 3-fluorobenzyl bromide] was converted to the title compound (8.9 g, 100%) which was obtained as a white solid. MS: m/e=245.0 ($M^+$).

b) 2-Fluoro-4-(4-fluoro-benzyloxy)-benzoic acid

As described for example 1b, 2-fluoro-4-(4-fluoro-benzyloxy)-benzonitrile (8.9 g, 36 mmol) was converted to the title compound (1.6 g, 16%) which was obtained as a white solid. MS: m/e=263.1 ($M-H^-$).

c) 2-[4-(4-Fluorobenzyloxy)-2-fluoro-benzamido]acetamide

As described for example 2, 2-fluoro-4-(4-fluoro-benzyloxy)-benzoic acid (150 mg, 0.6 mmol) [instead of 2-fluoro-4-(3-fluoro-benzyloxy)-benzoic acid] was converted to the title compound (113 mg, 62%) which was obtained as a white solid. MS: m/e=321.2 ($M+H^+$).

EXAMPLE 11

(S)-N-(1-Carbamoyl-ethyl)-2-fluoro-4-(4-fluoro-benzyloxy)-benzamide

As described for example 10c, 2-fluoro-4-(4-fluoro-benzyloxy)-benzoic acid (150 mg, 0.6 mmol) [using H-alanine-$NH_2$ HCl instead of glycinamide HCl] was converted to the title compound (188 mg, 100%) which was obtained as a white solid. MS: m/e=333.2 ($M+H^+$).

EXAMPLE 12

(S)-N-(1-Carbamoyl-ethyl)-2-fluoro-4-(4-trifluoromethyl-benzyloxy)-benzamide a) 2-Fluoro-4-(4-trifluoromethyl-benzyloxy)-benzonitrile As described for example 1a, 2-fluoro-4-hydroxy-benzonitrile (2.6 g, 19 mmol) [using 3-trifluorobenzyl bromide instead of 3-fluorobenzylbromide] was converted to the title compound (5.6 g, 100%) which was obtained as a white solid. MS: m/e=295.0 (M$^+$).

b) 2-Fluoro-4-(4-trifluoromethyl-benzyloxy)-benzoic acid

As described for example 1b, 2-fluoro-4-(4-trifluoromethyl-benzyloxy)-benzonitrile (5.6 g, 19 mmol) was converted to the title compound (400 mg, 5%) which was obtained as a white solid. MS: m/e=313.0 (M−H$^-$)

c) (S)-N-(1-Carbamoyl-ethyl)-2-fluoro-4-(4-trifluoromethyl-benzyloxy)-benzamide

As described for example 1c, 2-fluoro-4-(4-trifluoromethyl-benzyloxy)-benzoic acid (200 mg, 0.6 mmol) [instead of 2-fluoro-4-(3-fluoro-benzyloxy)-benzoic acid] was converted to the title compound (39 mg, 16%) which was obtained as a white solid.

MS: m/e=385.1 (M+H$^+$).

EXAMPLE 13

(S)-4-(3,5-Bis-trifluoromethyl-benzyloxy)-N-carbamoylmethyl-2-fluoro-benzamide a) 4-(3,5-Bis-trifluoromethyl-benzyloxy)-2-fluoro-benzonitrile As described for example 1a, 2-fluoro-4-hydroxy-benzonitrile (1.5 g, 10.5 mmol) [using 3,5-bis(trifluoromethyl)benzylbromide instead of 3-fluorobenzylbromide] was converted to the title compound (3.8 g, 99%) which was obtained as a white solid. MS: m/e=363.0 (M$^+$).

b) 4-(3,5-Bis-trifluoromethyl-benzyloxy)-2-fluoro-benzoic acid

As described for example 1b, 4-(3,5-bis-trifluoromethyl-benzyloxy)-2-fluoro-benzonitrile (3.8 g, 10.5 mmol) was converted to the title compound (1.7 g, 37%) which was obtained as a white solid. MS: m/e=380.9 (M−H$^-$).

c) (S)-4-(3,5-Bis-trifluoromethyl-benzyloxy)-N-carbamoylmethyl-2-fluoro-benzamide As described for example 2,4-(3,5-bis-trifluoromethyl-benzyloxy)-2-fluoro-benzoic acid (150 mg, 0.4 mmol) [instead of 2-fluoro-4-(3-fluoro-benzyloxy)-benzoic acid] was converted to the title compound (63 mg, 37%) which was obtained as a white solid. MS: m/e=439.1 (M+H$^+$).

EXAMPLE 14

(S)-4-(3,5-Bis-trifluoromethyl-benzyloxy)-N-(1-carbamoyl-ethyl)-2-fluoro-benzamide As described for example 1c, 4-(3,5-bis-trifluoromethyl-benzyloxy)-2-fluoro-benzoic acid (150 mg, 0.4 mmol) [instead of 2-fluoro-4-(3-fluoro-benzyloxy)-benzoic acid] was converted to the title compound (45 mg, 23%) which was obtained as a white solid. MS: m/e=453.2 (M+H$^+$).

EXAMPLE 15

2-[4-Benzyloxy-2-fluoro-benzamido]acetamide a) 4-Benzyloxy-2-fluoro-benzonitrile As described for example 1a, 2-fluoro-4-hydroxy-benzonitrile (9.7 g, 71 mmol) was converted to the title compound (15.0 g, 93%) (using benzyl bromide instead of 3-fluorobenzyl bromide) which was obtained as white crystals after recrystallisation from cyclohexane. MS: m/e= 227.2 (M$^+$).

b) 4-Benzyloxy-2-fluoro-benzoic acid

As described for example 1b, 4-benzyloxy-2-fluoro-benzonitrile (14.7 g, 65 mmol) was converted to the title compound (12.4 g, 78%) which was obtained as white crystals after recrystallisation from cyclohexane. MS: m/e= 246.2 (M$^+$).

c) 2-[4-Benzyloxy-2-fluoro-benzamido]acetamide

As described for example 2, 4-benzyloxy-2-fluoro-benzoic acid (300 mg, 1.2 mmol) was converted to the title compound (174 mg, 47%) which was obtained as a white solid. MS: m/e=303.3 (M+H$^+$).

EXAMPLE 16

4-Benzyloxy-N-cyanomethyl-2-fluoro-benzamide

As described for example 3, 4-benzyloxy-2-fluoro-benzoic acid (200 mg, 0.8 mmol) was converted to the title compound (205 mg, 89%) which was obtained as a light brown solid. MS: m/e=285.2 (M+H$^+$).

EXAMPLE 17

4-Benzyloxy-2-fluoro-N-(2-methoxy-ethyl)-benzamide

As described for example 4, 4-benzyloxy-2-fluoro-benzoic acid (200 mg, 0.8 mmol) was converted to the title compound (151 mg, 61%) which was obtained as a white solid. MS: m/e=304.3 (M+H$^+$).

EXAMPLE 18

(S)-N-(1-Carbamoyl-ethyl)-3-fluoro-4-(4-fluoro-benzyloxy)-benzamide a) 3-Fluoro-4-(4-fluoro-benzyloxy)-benzoic acid 4-fluoro-benzyl ester A mixture of 3-fluoro-4-hydroxybenzoic acid (4.68 g, 30 mmol), 4-fluorobenzyl bromide (17.0 g, 90 mmol) and potassium carbonate (8.3 g, 60 mmol) in THF:water (1:1, 100 mL) was heated at 65° C. for 48 h. After cooling to room temperature the mixture was extracted with ethyl acetate (2×100 mL) and the combined extracts washed with brine (100 mL) and dried over sodium sulfate. Filtration and evaporation gave a residue which was crystallised from ether:heptane to afford the title compound (8.4 g, 75%) as a white solid. MS: m/e=372.0 (M$^+$).

b) 3-Fluoro-4-(4-fluoro-benzyloxy)-benzoic acid

A mixture of 3-fluoro-4-(4-fluoro-benzyloxy)-benzoic acid 4-fluoro-benzyl ester (8.1 g, 22 mmol) and potassium hydroxide (6.1 g, 109 mmol) in water:dioxane (4:1, 150 mL) was heated at 100° C. for 12 h. After cooling to room temperature the mixture was acidified to pH 3 with HCl and the mixture was extracted with ethyl acetate (2×100 mL) and the combined extracts washed with brine (100 mL) and dried over sodium sulfate. Filtration and half evaporation gave a precipitate which was filtered off and crystallised from ethyl acetate:heptane to afford the title compound (4.9 g, 85%) as a white solid. MS: m/e=263.0 (M−H$^-$).

c) (S)-N-(1-Carbamoyl-ethyl)-3-fluoro-4-(4-fluoro-benzyloxy)-benzamide

As described for example 9, 3-fluoro-4-(4-fluoro-benzyloxy)-benzoic acid (264 mg, 1.0 mmol) [instead of 2-fluoro-4-(3-fluoro-benzyloxy)-benzoic acid] was converted to the title compound (240 mg, 72%) [using H-alanine-NH$_2$ HCl instead of H-D-alanine-NH$_2$ HCl] which was obtained as a white solid. MS: m/e=335.2 (M+H$^+$).

EXAMPLE 19

2-[4-(4-Fluorobenzyloxy)-3-fluoro-benzamido]acetamide

As described for example 18c, 3-fluoro-4-(4-fluoro-benzyloxy)-benzoic acid (200 mg, 0.8 mmol) was converted to the title compound (224 mg, 92%) [using glycinamide HCl instead of H-D-alanine-NH$_2$ HCl] which was obtained as a white solid. MS: m/e=321.2 (M+H$^+$).

EXAMPLE 20

(S)-N-(1-Carbamoyl-2-hydroxy-ethyl)-3-fluoro-4-(4-fluoro-benzyloxy)-benzamide

As described for example 18c, 3-fluoro-4-(4-fluoro-benzyloxy)-benzoic acid (200 mg, 0.8 mmol) was converted to the title compound (235 mg, 89%) [using H-Ser-NH$_2$ HCl instead of H-D-alanine-NH$_2$ HCl] which was obtained as a white solid. MS: m/e=351.2 (M+H$^+$).

EXAMPLE 21

N-Cyanomethyl-3-fluoro-4-(4-fluoro-benzyloxy)-benzamide

As described for example 18c, 3-fluoro-4-(4-fluoro-benzyloxy)-benzoic acid (200 mg, 0.8 mmol) was converted to the title compound (183 mg, 80%) [using aminoacetonitrile HCl instead of H-D-alanine-NH$_2$ HCl] which was obtained as a white solid after purification by chromatography (SiO$_2$, CH$_2$Cl$_2$:2N NH$_3$/MeOH 99:1 to 9:1). MS: m/e=303.3 (M+H$^+$).

EXAMPLE 22

3-Fluoro-4-(4-fluoro-benzyloxy)-N-(2-methoxy-ethyl)-benzamide

As described for example 18c, 3-fluoro-4-(4-fluoro-benzyloxy)-benzoic acid (264 mg, 1.0 mmol) was converted to the title compound (280 mg, 87%) [using 2-methoxy ethylamine instead of H-D-alanine-NH$_2$ HCl] which was obtained as a white solid after purification by chromatography (SiO$_2$, CH$_2$Cl$_2$:2N NH$_3$/MeOH 99:1 to 9:1). MS: m/e=322.3 (M+H$^+$).

EXAMPLE 23

N-(2-Amino-ethyl)-3-fluoro-4-(4-fluoro-benzyloxy)-benzamide 1:1 hydrochloride a) 2-[3-Fluoro-4-(4-fluoro-benzyloxy)-benzoylamino]-ethyl}-carbamic acid tert-butyl ester As described for example 7a, 3-fluoro-4-(4-fluoro-benzyloxy)-benzoic acid (200 mg, 0.8 mmol) [instead of 2-fluoro-4-(3-fluoro-benzyloxy)-benzoic acid] was converted to the title compound (400 mg, 99%) which was obtained as a white solid after purification by chromatography (SiO$_2$, CH$_2$Cl$_2$:2N NH$_3$/MeOH 99:1 to 9:1). MS: m/e=407.4 (M+H$^+$).

b) N-(2-Amino-ethyl)-3-fluoro-4-(4-fluoro-benzyloxy)-benzamide 1:1 hydrochloride As described for example 7b, 2-[3-fluoro-4-(4-fluoro-benzyloxy)-benzoylamino]-ethyl}-carbamic acid tert-butyl ester (400 mg, 0.1 mmol) was converted to the title compound (239 mg, 92%) which was obtained as a white solid. MS: m/e=307.2 (M+H$^+$).

EXAMPLE 24

N-(3-Amino-propyl)-3-fluoro-4-(4-fluoro-benzyloxy)-benzamide 1:1 hydrochloride

As described for example 18c, 3-fluoro-4-(4-fluoro-benzyloxy)-benzoic acid (200 mg, 0.8 mmol) was converted to the tert-butylcarbamate protected title compound [using N-(3-aminopropyl)carbamic acid tert-butylester instead of H-D-alanine-NH$_2$ HCl] which was obtained as a white solid. This was then reacted as described for example 7b, to afford the title compound (243 mg, 90%) as a white solid. MS: m/e=320.9 (M+H$^+$).

EXAMPLE 25

2-[4-(3-Fluorobenzyloxy)-3-fluoro-benzamido]acetamide a) 3-Fluoro-4-(3-fluoro-benzyloxy)-benzoic acid 3-fluoro-benzyl ester As described for example 18a, 3-fluoro-4-hydroxybenzoic acid (3.6 g, 23.1 mmol) was converted to the title compound (6.9 g, 81%) [using 3-fluorobenzyl bromide instead of 4-fluorobenzyl bromide] which was obtained as a white solid. MS: m/e=372.1 (M$^+$).

b) 3-Fluoro-4-(3-fluoro-benzyloxy)-benzoic acid

As described for example 18b, 3-fluoro-4-(3-fluoro-benzyloxy)-benzoic acid 3-fluoro-benzyl ester (6.9 g, 18.6 mmol) [instead of 3-fluoro-4-(4-fluoro-benzyloxy)-benzoic acid 4-fluoro-benzyl ester] was converted to the title compound (4.4 g, 90%) which was obtained as a white solid. MS: m/e=263.0 (M$^+$).

c) 2-[4-(3-Fluorobenzyloxy)-3-fluoro-benzamido]acetamide

As described for example 19, 3-fluoro-4-(3-fluoro-benzyloxy)-benzoic acid (200 mg, 0.8 mmol) [instead of 3-fluoro-4-(4-fluoro-benzyloxy)-benzoic acid] was converted to the title compound (216 mg, 89%) which was obtained as a white solid. MS: m/e=321.3 (M+H$^+$).

EXAMPLE 26

(S)-N-(1-Carbamoyl-ethyl)-3-fluoro-4-(3-fluoro-benzyloxy)-benzamide

As described for example 25, 3-fluoro-4-(3-fluoro-benzyloxy)-benzoic acid (200 mg, 0.8 mmol) was converted to the title compound (225 mg, 89%) [using H-alanine-NH$_2$ HCl instead of glycinamide HCl] which was obtained as a white solid. MS: m/e=335.2 (M+H$^+$).

EXAMPLE 27

(R)-N-(1-Carbamoyl-ethyl)-3-fluoro-4-(3-fluoro-benzyloxy)-benzamide

As described for example 25c, 3-fluoro-4-(3-fluoro-benzyloxy)-benzoic acid (200 mg, 0.8 mmol) was converted to the title compound (240 mg, 95%) [using H-D-alanine-NH$_2$ HCl instead of glycinamide HCl] which was obtained as a white solid. MS: m/e=335.2 (M+H$^+$).

EXAMPLE 28

(S)-N-(1-Carbamoyl-2-hydroxy-ethyl)-3-fluoro-4-(3-fluoro-benzyloxy)-benzamide

As described for example 25c, 3-fluoro-4-(3-fluoro-benzyloxy)-benzoic acid (200 mg, 0.8 mmol) was converted to the title compound (116 mg, 41%) [using H-Ser-NH$_2$ HCl instead of glycinamide HCl] which was obtained as a white solid after purification by HPLC (Waters Xterra RP18 (5 µM,×50×19 mm) eluting with MeCN 0.1% TFA, Water. MS: m/e=351.2 (M+H$^+$).

EXAMPLE 29

N-Cyanomethyl-3-fluoro-4-(3-fluoro-benzyloxy)-benzamide

As described for example 25c, 3-fluoro-4-(3-fluoro-benzyloxy)-benzoic acid (200 mg, 0.8 mmol) was converted to the title compound (208 mg, 91%) [using aminoacetonitrile HCl instead of glycinamide HCl] which was obtained as a white solid. MS: m/e=303.1 (M+H$^+$).

EXAMPLE 30

N-(2-Amino-ethyl)-3-fluoro-4-(3-fluoro-benzyloxy)-benzamide 1:1 hydrochloride a) {2-[3-Fluoro-4-(3-fluoro-benzyloxy)-benzoylamino]-ethyl}-carbamic acid tert-butyl ester As described for example 1c, 2-fluoro-4-(3-fluoro-benzyloxy)-benzoic acid (300 mg, 1.1 mmol) [instead of 2-fluoro-4-(3-fluoro-benzyloxy)-benzoic acid] was converted to the title compound (403 mg, 87%) which was obtained as a white solid. MS: m/e=407.3 (M+H$^+$).

b) N-(2-Amino-ethyl)-2-fluoro-4-(3-fluoro-benzyloxy)-benzamide 1:1 hydrochloride As described for example 9b, {2-[3-fluoro-4-(3-fluoro-benzyloxy)-benzoylamino]-ethyl}-carbamic acid tert-butyl ester (373 mg, 0.9 mmol) [instead of 2-[2-fluoro-4-(3-fluoro-benzyloxy)-benzoylamino]-ethyl}-carbamic acid tert-butyl ester] was converted to the title compound (299 mg, 95%) which was obtained as a white solid. MS: m/e= 341.5 (M–H$^-$

EXAMPLE 31

2-[4-(4-Trifluoromethylbenzyloxy)-3-fluoro-benzamido]acetamide a) 3-Fluoro-4-(4-trifluoromethyl-benzyloxy)-benzoic acid 4-trifluoromethyl-benzyl ester As described for example 18a, 3-fluoro-4-hydroxybenzoic acid (2.5 g, 16 mmol) [using 4-(trifluoromethyl)-benzyl bromide instead of 4-fluorobenzyl bromide] was converted to the title compound (5.3 g, 69%) which was obtained as a white solid. MS: m/e=472.1 (M$^+$).

b) Fluoro-4-(4-trifluoromethyl-benzyloxy)-benzoic acid

As described for example 18b, 3-fluoro-4-(4-trifluoromethyl-benzyloxy)-benzoic acid 4-trifluoromethyl-benzyl ester (5.3 g, 11 mmol) [instead of 3-fluoro-4-(4-fluoro-benzyloxy)-benzoic acid 4-trifluoromethyl-benzyl ester] was converted to the title compound (3.1 g, 90%) which was obtained as a white solid. MS: m/e=312.9 (M–H$^-$).

c) 2-[4-(4-Trifluoromethylbenzyloxy)-3-fluoro-benzamido]acetamide

As described for example 9, 3-fluoro-4-(4-trifluoromethyl-benzyloxy)-benzoic acid (200 mg, 0.6 mmol) [instead of 2-fluoro-4-(3-fluoro-benzyloxy)-benzoic acid] was converted to the title compound (208 mg, 88%) [using glycinamide HCl instead of H-D-alanine-NH$_2$ HCl] which was obtained as a white solid. MS: m/e=371.2 (M+H$^+$).

EXAMPLE 32

(S)-N-(1-Carbamoyl-ethyl)-3-fluoro-4-(4-trifluoromethyl-benzyloxy)-benzamide

As described for example 31c, 3-fluoro-4-(4-trifluoromethyl-benzyloxy)-benzoic acid (200 mg, 0.6 mmol) was converted to the title compound (214 mg, 88%) [using H-alanine-NH$_2$ HCl instead of glycinamide HCl] which was obtained as a white solid. MS: m/e=385.2 (M+H$^+$).

EXAMPLE 33

(R)-N-(1-Carbamoyl-ethyl)-3-fluoro-4-(4-trifluoromethyl-benzyloxy)-benzamide

As described for example 31c, 3-fluoro-4-(4-trifluoromethyl-benzyloxy)-benzoic acid (200 mg, 0.6 mmol) was converted to the title compound (213 mg, 87%) [using H-D-alanine-NH$_2$ HCl instead of glycinamide HCl] which was obtained as a white solid. MS: m/e=385.2 (M+H$^+$).

EXAMPLE 34

(S)-N-(1-Carbamoyl-2-hydroxy-ethyl)-3-fluoro-4-(4-trifluoromethyl-benzyloxy)-benzamide As described for example 31c, 3-fluoro-4-(4-trifluoromethyl-benzyloxy)-benzoic acid (200 mg, 0.6 mmol) was converted to the title compound (124 mg, 49%) [using H-Ser-NH$_2$ HCl instead of glycinamide HCl] which was obtained as a white solid after purification by HPLC (Waters Xterra RP18 (5 µM,×50×19 mm) eluting with MeCN 0.1% TFA, Water. MS: m/e=401.4 (M+H$^+$).

EXAMPLE 35

N-Cyanomethyl-3-fluoro-4-(4-trifluoromethyl-benzyloxy)-benzamide

As described for example 31c, 3-fluoro-4-(4-trifluoromethyl-benzyloxy)-benzoic acid (200 mg, 0.6 mmol) was converted to the title compound (206 mg, 92%) [using aminoacetonitrile HCl instead of glycinamide HCl] which was obtained as a white solid. MS: m/e=353.2 (M+H$^+$).

EXAMPLE 36

N-(2-Amino-ethyl)-3-fluoro-4-(4-trifluoromethyl-benzyloxy)-benzamide 1:1 hydrochloride a) {2-[3-Fluoro-4-(4-trifluoromethyl-benzyloxy)-benzoylamino]-ethyl}-carbamic acid tert-butyl ester As described for example 31c, 3-fluoro-4-(4-trifluoromethyl-benzyloxy)-benzoic acid (300 mg, 1.0 mmol) was converted to the title compound (384 mg, 88%) [using tert-butyl-N-(2-aminoethyl)carbamate instead of glycinamide HCl] which was obtained as a white solid. MS: m/e=457.5 (M+H$^+$).

b) N-(2-Amino-ethyl)-3-fluoro-4-(4-trifluoromethyl-benzyloxy)-benzamide 1:1 hydrochloride As described for example 7b, {2-[3-fluoro-4-(4-trifluoromethyl-benzyloxy)-benzoylamino]-ethyl}-carbamic acid tert-butyl ester (357 mg, 0.8 mmol) [instead of 2-[2-fluoro-4-(3-fluoro-benzyloxy)-benzoylamino]-ethyl}-carbamic acid tert-butyl ester] was converted to the title compound (278 mg, 100%) which was obtained as a white solid. MS: m/e=357.2 (M+H$^+$).

EXAMPLE 37

(S)-N-(1-Carbamoyl-ethyl)-2,6-difluoro-4-(4-fluoro-benzyloxy)-benzamide a) 3,5-Difluoro-(4-fluoro-benzyloxy)-benzene A mixture of 3,5-difluorophenol (1 1.0 g, 84.6 mmol), 4-fluorobenzylbromide (16.5 g, 84.6 mmol) and potassium carbonate (12.7 g, 92.2 mmol) in acetone (50 mL) was heated under reflux for 6 h. After cooling to room temperature, the mixture was filtered and the filtrate evaporated. The residue was dissolved in diethyl ether, washed with sodium cabonate (saturated solution), dried over sodium sulfate, filtered and evaporated to leave the title compound (20.8 g, 96%) as a light yellow liquid. MS: m/e=238.1 (M$^+$).

b) 2,6-Difluoro-4-(4-fluoro-benzyloxy)-benzoic acid

BuLi (1.6 M in hexane, 27.1 mL, 43.4 mmol) was added to a solution of 3,5-difluoro-(4-fluoro-benzyloxy)-benzene (10.5 g, 41.4 mmol) in dry THF at −78° C., under Argon, and the reaction mixture maintained at this temperature for 1 h whereupon carbon dioxide gas was bubbled into the solution over a 10 min period. The reaction mixture was then warmed up to room temperature and water added. The resulting mixture was extracted with diethyl ether. The aqueous phase was adjusted to pH 2 with HCl and extracted with ethyl acetate. The combined ethyl acetate layers were washed with HCl (0.1 N), then dried over sodium sulfate, filtered and evaporated to leave a white solid. This was triturated with pentane-diethyl ether to afford the title compound (6.8 g, 59%) as a white solid. MS: m/e=280.9 (M−H⁻).

c) (S)-N-(1-Carbamoyl-ethyl)-2,6-difluoro-4-(4-fluoro-benzyloxy)-benzamide

As described for example 1c, 2,6-difluoro-4-(4-fluoro-benzyloxy)-benzoic acid (282 mg, 1 mmol) was converted to the title compound (237 mg, 65%) which was obtained as a white solid. MS: m/e=353.2 (M+H⁺).

EXAMPLE 38

(R)-N-(1-Carbamoyl-ethyl)-2,6-difluoro-4-(4-fluoro-benzyloxy)-benzamide

As described for example 9, 2,6-difluoro-4-(4-fluoro-benzyloxy)-benzoic acid (282 mg, 1 mmol) was converted to the title compound (264 mg, 71%) which was obtained as a white solid. MS: m/e=353.2 (M+H⁺).

EXAMPLE 39

N-Carbamoylmethyl-2,6-difluoro-4-(4-fluoro-benzyloxy)-benzamide

As described for example 2, 2,6-difluoro-4-(4-fluoro-benzyloxy)-benzoic acid (282 mg, 1 mmol) was converted to the title compound (292 mg, 85%) which was obtained as a white solid. MS: m/e=339.1 (M+H⁺).

EXAMPLE 40

N-Cyanomethyl-2,6-difluoro-4-(4-fluoro-benzyloxy)-benzamide

As described for example 3, 2,6-difluoro-4-(4-fluoro-benzyloxy)-benzoic acid (282 mg, 1 mmol) was converted to the title compound (279 mg, 87%) which was obtained as a white solid. MS: m/e=321.2 (M+H⁺).

EXAMPLE 41

2,6-Difluoro-4-(4-fluoro-benzyloxy)-N-(2-methoxy-ethyl)-benzamide

As described for example 6, 2,6-difluoro-4-(4-fluoro-benzyloxy)-benzoic acid (282 mg, 1 mmol) was converted to the title compound (306 mg, 90%) which was obtained as a white solid. MS: m/e=340.2 (M+H⁺).

EXAMPLE 42

(S)-N-(1-Carbamoyl-2-hydroxy-ethyl)-2,6-difluoro-4-(4-fluoro-benzyloxy)-benzamide As described for example 5, 2,6-difluoro-4-(4-fluoro-benzyloxy)-benzoic acid (282 mg, 1 mmol) was converted to the title compound (191 mg, 52%) which was obtained as a white solid. MS: m/e=369.2 (M+H⁺).

EXAMPLE 43

N-(2-Amino-ethyl)-2,6-difluoro-4-(4-fluoro-benzyloxy)-benzamide 1:1 hydrochloride As described for example 7, 2,6-difluoro-4-(4-fluoro-benzyloxy)-benzoic acid (282 mg, 1 mmol) was converted to the title compound (179 mg, 72%) which was obtained as a white solid. MS: m/e=325.2 (M−Cl⁺).

EXAMPLE 44

2,6-Difluoro-4-(4-fluoro-benzyloxy)-N-(2-hydroxy-ethyl)-benzamide

As described for example 8, 2,6-difluoro-4-(4-fluoro-benzyloxy)-benzoic acid (282 mg, 1 mmol) was converted to the title compound (241 mg, 74%) which was obtained as a white solid. MS: m/e=326.3 (M+H⁺).

EXAMPLE 45

(S)-2,6-Difluoro-4-(4-fluoro-benzyloxy)-N-(2-hydroxy-1-methyl-ethyl)-benzamide

As described for example 1c, 2,6-difluoro-4-(4-fluoro-benzyloxy)-benzoic acid (282 mg, 1 mmol) was converted to the title compound (205 mg, 59%) [using L-alaninol instead of H-alanine-NH₂ HCl] which was obtained as a white solid. MS: m/e=340.2 (M+H⁺).

EXAMPLE 46

(R)-2,6-Difluoro-4-(4-fluoro-benzyloxy)-N-(2-hydroxy-1-methyl-ethyl)-benzamide

As described for example 45, 2,6-difluoro-4-(4-fluoro-benzyloxy)-benzoic acid (282 mg, 1 mmol) was converted to the title compound (218 mg, 62%) [using D-alaninol instead of L-alaninol] which was obtained as a white solid. MS: m/e=340.2 (M+H⁺).

EXAMPLE 47

(S)-N-(1-Carbamoyl-ethyl)-2,6-difluoro-4-(3-fluoro-benzyloxy)-benzamide a) 3,5-Difluoro-(3-fluoro-benzyloxy)-benzene As described for example 37a, 3,5-difluorophenol (10 g, 76.9 mmol) was converted to the to the title compound (18.1 g, 97%) [using 3-fluorobenzyl bromide instead of 4-fluorobenzyl bromide] which was obtained as a light yellow liquid. MS: m/e=238.1 (M+H⁺).

b) 2,6-Difluoro-4-(3-fluoro-benzyloxy)-benzoic acid

As described for example 37b, 3,5-difluoro-(3-fluoro-benzyloxy)-benzene (13 g, 54.6 mmol) was converted to the title compound (6.3 g, 41%) which was obtained as a white solid. MS: m/e=280.9 (M+H⁺).

c) (S)-N-(1-Carbamoyl-ethyl)-2,6-difluoro-4-(3-fluoro-benzyloxy)-benzamide

As described for example 37c, 2,6-difluoro-4-(3-fluoro-benzyloxy)-benzoic acid (250 mg, 0.89 mmol) was converted to the title compound (226 mg, 72%) which was obtained as a white solid. MS: m/e=353.2 (M+H⁺).

EXAMPLE 48

(R)-N-(1-Carbamoyl-ethyl)-2,6-difluoro-4-(3-fluoro-benzyloxy)-benzamide

As described for example 38, 2,6-difluoro-4-(3-fluoro-benzyloxy)-benzoic acid (250 mg, 0.89 mmol) was converted to the title compound (224 mg, 72%) which was obtained as a white solid. MS: m/e=353.2 (M+H⁺).

EXAMPLE 49

N-Carbamoylmethyl-2,6-difluoro-4-(3-fluoro-benzyloxy)-benzamide

As described for example 39, 2,6-difluoro-4-(3-fluoro-benzyloxy)-benzoic acid (250 mg, 0.89 mmol) was con-

EXAMPLE 50

N-Cyanomethyl-2,6-difluoro-4-(3-fluoro-benzyloxy)-benzamide

As described for example 40, 2,6-difluoro-4-(3-fluoro-benzyloxy)-benzoic acid (250 mg, 0.89 mmol) was converted to the title compound (245 mg, 86%) which was obtained as a white solid. MS: m/e=321.2 (M+H$^+$).

EXAMPLE 51

2,6-Difluoro-4-(3-fluoro-benzyloxy)-N-(2-methoxy-ethyl)-benzamide

As described for example 41, 2,6-difluoro-4-(3-fluoro-benzyloxy)-benzoic acid (250 mg, 0.89 mmol) was converted to the title compound (264 mg, 88%) which was obtained as a white solid. MS: m/e=340.2 (M+H$^+$).

EXAMPLE 52

(S)-N-(1-Carbamoyl-2-hydroxy-ethyl)-2,6-difluoro-4-(3-fluoro-benzyloxy)-benzamide As described for example 42, 2,6-difluoro-4-(3-fluoro-benzyloxy)-benzoic acid (250 mg, 0.89 mmol) was converted to the title compound (234 mg, 72%) which was obtained as a white solid. MS: m/e=369.2 (M+H$^+$).

EXAMPLE 53

N-(2-Amino-ethyl)-2,6-difluoro-4-(3-fluoro-benzyloxy)-benzamide (1:1) hydrochloride As described for example 43, 2,6-difluoro-4-(3-fluoro-benzyloxy)-benzoic acid (250 mg, 0.89 mmol) was converted to the title compound (264 mg, 89%) which was obtained as a white solid. MS: m/e=325.3 (M−Cl$^+$).

EXAMPLE 54

2,6-Difluoro-4-(3-fluoro-benzyloxy)-N-(2-hydroxy-ethyl)-benzamide

As described for example 44, 2,6-difluoro-4-(3-fluoro-benzyloxy)-benzoic acid (250 mg, 0.89 mmol) was converted to the title compound (165 mg, 57%) which was obtained as a white solid. MS: m/e=326.3 (M+H$^+$).

EXAMPLE 55

(S)-2,6-Difluoro-4-(3-fluoro-benzyloxy)-N-(2-hydroxy-1-methyl-ethyl)-benzamide

As described for example 45, 2,6-difluoro-4-(3-fluoro-benzyloxy)-benzoic acid (250 mg, 0.89 mmol) was converted to the title compound (120 mg, 40%) which was obtained as a white solid. MS: m/e=340.2 (M+H$^+$).

EXAMPLE 56

(R)-2,6-Difluoro-4-(3-fluoro-benzyloxy)-N-(2-hydroxy-1-methyl-ethyl)-benzamide

As described for example 46, 2,6-difluoro-4-(3-fluoro-benzyloxy)-benzoic acid (250 mg, 0.89 mmol) was converted to the title compound (100 mg, 33%) which was obtained as a white solid. MS: m/e=340.2 (M+H$^+$).

EXAMPLE A

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution may have the following composition and is manufactured in usual manner:

| Active substance | 1.0 mg |
|---|---|
| 1 N HCl | 20.0 µl |
| acetic acid | 0.5 mg |
| NaCl | 8.0 mg |
| phenol | 10.0 mg |

| 1 N NaOH | q.s. ad pH 5 |
| H₂O | q.s. ad 1 ml |

What is claimed is:

1. A compound of the formula

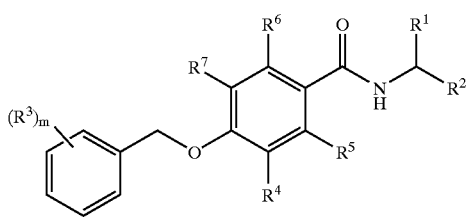

wherein
$R^1$ is hydrogen, $(C_1-C_6)$-alkyl or hydroxy-$(C_1-C_6)$-alkyl;
$R^2$ is $(C_1-C_6)$-alkyl,
—CO—$NR^8R^9$,
—$(CH_2)_n$—$NR^8R^9$,
—$(CH_2)_p$—$OR^8$, or
—$(CH_2)_n$—CN;
$R^3$ is selected from hydrogen halogen, halogen-$(C_1-C_6)$-alkyl, cyano, $(C_1-C_6)$-alkoxy or halogen-$(C_1-C_6)$-alkoxy;
$R^4, R^5, R^6$ and $R^7$ are hydrogen or fluoro, wherein at least one of $R^4, R^5, R^6$ and $R^7$ is fluoro;
$R^8$ and $R^9$ are each independently hydrogen or $(C_1-C_6)$-alkyl;
m is 1, 2 or 3;
n is 0, 1, 2 or 3; and
p is 1 or 2;
or a pharmaceutically acceptable salt thereof.

2. A compound of formula I according to claim 1, wherein $R^2$ is $(C_1-C_6)$-alkyl.

3. A compound of formula I according to claim 1, wherein $R^2$ is —CO—$NR^8R^9$ and $R^8$ and $R^9$ are each independently hydrogen or $(C_1-C_6)$-alkyl.

4. A compound of formula I according to claim 1, wherein $R^2$ is —$(CH_2)_n$—$NR^8R^9$, $R^8$ and $R^9$ are each independently hydrogen or $(C_1-C_6)$-alkyl and n is 0, 1, 2 or 3.

5. A compound of formula I according to claim 1, wherein $R^2$ is —$(CH_2)_p$—$OR^8$, $R^8$ is hydrogen or $(C_1-C_6)$-alkyl, and p is 1 or 2.

6. A compound of formula I according to claim 1, wherein $R^2$ is —$(CH_2)_n$—CN and n is 0, 1, 2 or 3.

7. A compound of formula I according to claim 1, wherein $R^3$ is halogen, halogen-$(C_1-C_6)$-alkyl cyano, $(C_1-C_6)$-alkoxy or halogen-$(C_1-C_6)$-alkoxy.

8. A compound according to claim 7, wherein $R^3$ is halogen, halogen-$(C_1-C_6)$-alkyl or halogen-$(C_1-C_6)$-alkoxy.

9. A compound of formula I according to claim 7, wherein $R^3$ is $(C_1-C_6)$-alkoxy.

10. A compound of formula I according to claim 7, wherein $R^3$ is cyano.

11. A compound of formula I according to claim 1, wherein $R^3$ is hydrogen.

12. A compound of formula I according to claim 1, wherein $R^5$ is fluoro and $R^4, R^6$ and $R^7$ are hydrogen.

13. A compound of formula I according to claim 12, wherein $R^2$ is —CO—$NR^8R^9$ and $R^8$ and $R^9$ are each independently hydrogen or $(C_1-C_6)$-alkyl.

14. A compound of formula I according to claim 13, wherein $R^3$ is fluoro.

15. A compound of formula I according to claim 14, selected from the group consisting of
(S)-N-(1-carbamoyl-ethyl)-2-fluoro-4-(3-fluoro-benzyloxy)-benzamide,
2-[4-(3-fluorobenzyloxy)-2-fluoro-benzamido]acetamide,
(S)-N-(1-carbamoyl-2-hydroxy-ethyl)-2-fluoro-4-(3-fluoro-benzyloxy)-benzamide,
(R)-N-(1-carbamoyl-ethyl)-2-fluoro-4-(3-fluoro-benzyloxy)-benzamide,
2-[4-(4-fluorobenzyloxy)-2-fluoro-benzamido]acetamide, and
(S)-N-(1-carbamoyl-ethyl)-2-fluoro-4-(4-fluoro-benzyloxy)-benzamide.

16. A compound of formula I according to claim 13, wherein $R^3$ is trifluoromethyl.

17. A compound of formula I according to claim 16, selected from the group consisting of
(S)-N-(1-carbamoyl-ethyl)-2-fluoro-4-(4-trifluoromethyl-benzyloxy)-benzamide, and
(S)-4-(3,5-bis-trifluoromethyl-benzyloxy)-N-(1-carbamoyl-ethyl)-2-fluoro-benzamide.

18. A compound of formula I according to claim 12, wherein $R^2$ is —$(CH_2)_p$—$OR^8$, $R^8$ is hydrogen or $(C_1-C_6)$-alkyl and p is 1 or 2.

19. A compound of formula I according to claim 18, selected from the group consisting of
(S)-2-fluoro-4-(3-fluoro-benzyloxy)-N-(2-methoxy-1-methyl-ethyl)-benzamide,
2-fluoro-4-(3-fluoro-benzyloxy)-N-(2-methoxy-ethyl)-benzamide, and
2-fluoro-4-(3-fluoro-benzyloxy)-N-(2-hydroxy-ethyl)-benzamide.

20. A compound of formula I according to claim 12, wherein $R^2$ is —$(CH_2)_n$—$NR^8R^9$ and wherein $R^8$ and $R^9$ are each independently hydrogen or $(C_1-C_6)$-alkyl and n is 0, 1, 2 or 3.

21. A compound of formula I according to claim 12, wherein $R^2$ is —$(CH_2)_n$—CN and n is 0, 1, 2 or 3.

22. A compound of formula I according to claim 12, wherein $R^2$ is $(C_1-C_6)$-alkyl.

23. A compound of formula I according to claim 1, wherein $R^4$ is fluoro and $R^5, R^6$ and $R^7$ are hydrogen.

24. A compound of formula I according to claim 23, wherein $R^2$ is —CO—$NR^8R^9$ and $R^8$ and $R^9$ are each independently hydrogen or $(C_1-C_6)$-alkyl.

25. A compound of formula I according to claim 24, wherein $R^3$ is fluoro.

26. A compound of formula I according to claim 25, selected from the group consisting of
(S)-N-(1-carbamoyl-ethyl)-3-fluoro-4-(4-fluoro-benzyloxy)-benzamide,
2-[4-(4-fluorobenzyloxy)-3-fluoro-benzamido]acetamide,
(S)-N-(1-carbamoyl-2-hydroxy-ethyl)-3-fluoro-4-(4-fluoro-benzyloxy)-benzamide,
2-[4-(3-fluorobenzyloxy)-3-fluoro-benzamido]acetamide,
(S)-N-(1-carbamoyl-ethyl)-3-fluoro-4-(3-fluoro-benzyloxy)-benzamide,
(R)-N-(1-carbamoyl-ethyl)-3-fluoro-4-(3-fluoro-benzyloxy)-benzamide, and
(S)-N-(1-carbamoyl-2-hydroxy-ethyl)-3-fluoro-4-(3-fluoro-benzyloxy)-benzamide.

27. A compound of formula I according to claim 24, wherein $R^3$ is trifluoromethyl.

28. A compound of formula I according to claim 27, selected from the group consisting of
2-[4-(4-trifluoromethylbenzyloxy-3-fluoro-benzamido] acetamide, and
(S)-N-(1-carbamoyl-2-hydroxy-ethyl)-3-fluoro-4-(4-trifluoromethyl-benzyloxy)-benzamide.

29. A compound of formula I according to claim 23, wherein $R^2$ is —$(CH_2)_p$—$OR^8$, $R^8$ is hydrogen or $(C_1-C_6)$-alkyl and p is 1 or 2.

30. A compound of formula I according to claim 23, wherein $R^2$ is —$(CH_2)_n$—$NR^8R^9$ and wherein $R^8$ and $R^9$ are each independently hydrogen or $(C_1-C_6)$-alkyl and n is 0, 1, 2 or 3.

31. A compound of formula I according to claim 23, wherein $R^2$ is $(CH_2)_n$—CN and n is 0, 1, 2 or 3.

32. A compound of formula I according to claim 23, wherein $R^2$ is $(C_1-C_6)$-alkyl.

33. A compound of formula I according to claim 1, wherein $R^6$ is fluoro and $R^4$, $R^5$, and $R^7$ are hydrogen.

34. A compound of formula I according to claim 1, wherein $R^7$ is fluoro and $R^4$, $R^5$, and $R^6$ are hydrogen.

35. A compound of formula I according to claim 1, wherein at least two of $R^4$, $R^5$, $R^6$, and $R^7$ are fluoro.

36. A compound of formula I according to claim 35, wherein $R^4$ and $R^5$ are both fluoro and $R^6$ and $R^7$ are hydrogen.

37. A compound of formula I according to claim 36, selected from the group consisting of
(S)-N-(1-carbamoyl-ethyl)-2,6-difluoro-4-(4-fluoro-benzyloxy)-benzamide,
N-carbamoylmethyl-2,6-difluoro-4-(4-fluoro-benzyloxy)-benzamide,
N-cyanomethyl-2,6-difluoro-4-(4difluoro-benzyloxy)-benzamide,
2,6-difluoro-4-(4-fluoro-benzylox)-N-(2-methoxy-ethyl)-benzamide,
(S)-2,6-difluoro-4-(4-fluoro-benzyloxy)-N-(2-hydroxy-1-methyl-ethyl)-benzamide and
2,6-difluoro-4-(3-fluoro-benzylox)-N-(2-methoxy-ethyl)-benzamide.

38. A compound of formula I according to claim 1, wherein at least three of $R^4$, $R^5$, $R^6$, and $R^7$ are fluoro.

39. A compound of formula I according to claim 1, wherein $R^4$, $R^5$, $R^6$, and $R^7$ are fluoro.

40. A compound of formula I according to claim 1, selected from the group consisting of
N-Cyanomethyl-2-fluoro-4-(3-fluoro-benzyloxy)-benzamide;
N-(2-Amino-ethyl)-2-fluoro-4-(3fluoro-benzyloxy)-benzamide 1:1 hydrochloride;
(S)-4-(3,5-Bis-trifluoromethyl-benzyloxy)-N-carbamoylmethyl-2-fluoro-benzamide;
2-[4-Benzyloxy-2-fluoro-benzamido]acetamide;
4-Benzyloxy-N-cyanomethyl-2-fluoro-benzamide;
4-Benzyloxy-2-fluoro-N-(2-methoxy-ethyl)-benzamide;
N-Cyanomethyl-3-fluoro-4-(4-fluoro-benzyloxy)-benzamide;
3-Fluoro-4-(4-fluoro-benzyloxy)-N-(2-methoxy-ethyl)-benzamide;
N-(2-Amino-ethyl)-3-fluoro-4-(4fluoro-benzyloxy)-benzamide 1:1 hydrochloride;
N-(3-Amino-propyl)-3-fluoro-4-(4-fluoro-benzyloxy)-benzamide 1:1 hydrochloride;
N-Cyanomethyl-3-fluoro-4-(3-fluoro-benzyloxy)-benzamide; and
N-(2-Amino-ethyl)-3-fluoro-4-(3fluoro-benzyloxy)-benzamide 1:1 hydrochloride.

41. A compound of formula I according to claim 1, selected from the group consisting of
(S)-N-(1-Carbamoyl-ethyl)-3-fluoro-4-(4-trifluoromethyl-benzyloxy)-benzamide;
(R)-N-(1-Carbamoyl-ethyl)-3-fluoro-4-(4-trifluoromethyl-benzyloxy)-benzamide;
N-Cyanomethyl-3-fluoro-4-(4-trifluoromethyl-benzyloxy)-benzamide;
N-(2-Amino-ethyl)-3-fluoro-4-(4trifluoromethyl-benzyloxy)-benzamide 1:1 hydrochloride;
(R)-N-(1-Carbamoyl-ethyl)-2,6-difluoro-4-(4-fluoro-benzyloxy)-benzamide
(S)-N-(1-Carbamoyl-2-hydroxy-ethyl)-2,6difluoro-4-(4-fluoro-benzyloxy)-benzamide;
N-(2-Amino-ethyl)-2,6-difluoro-4-(4-fluoro-benzyloxy)-benzamide 1:1 hydrochloride;
2,6-Difluoro-4-(4-fluoro-benzyloxy)-N-(2-hydroxy-ethyl)-benzamide;
(R)-2,6-Difluoro-4-(4-fluoro-benzyloxy)-N-(2-hydroxy-1-methyl-ethyl)-benzamide;
(S)-N-(1-Carbamoyl-ethyl)-2,6-difluoro-4-(3-fluoro-benzyloxy)-benzamide; and
(R)-N-(1-Carbamoyl-ethyl)-2,6-fluoro-4-(3-fluoro-benzyloxy)-benzamide.

42. A compound of formula I according to claim 1, selected from the group consisting of
N-Carbamoylmethyl-2,6-difluoro-4-(3-fluoro-benzyloxy)-benzamide;
N-Cyanomethyl-2,6-difluoro-4-(3-fluoro-benzyloxy)-benzamide;
(S)-N-(1-Carbamoyl-2-hydroxy-ethyl)-2,6-difluoro-4-(3-fluoro-benzyloxy)-benzamide;
N-(2-Amino-ethyl)-2,6-difluoro-4-(3-fluoro-benzyloxy)-benzamide (1:1) hydrochloride;
2,6-Difluoro-4-(3-fluoro-benzyloxy)-N-(2-hydroxy-ethyl)-benzamide;
(S)-2,6-Difluoro-4-(3-fluoro-benzyloxy)-N-(2-hydroxy-1-methyl-ethyl)-benzamide; and
(R)-2,6-Difluoro-4-(3-fluoro-benzyloxy)-N-(2-hydroxy-1-methyl-ethyl)-benzamide.

43. A composition comprising one or more compounds of the formula

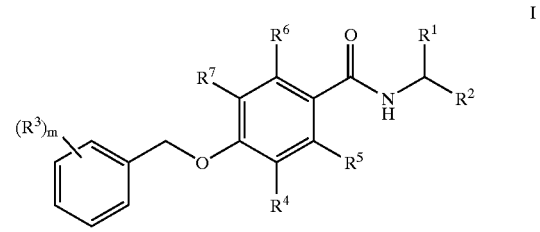

wherein
$R^1$ is hydrogen, $(C_1-C_6)$-alkyl or hydroxy-$(C_1-C_6)$-alkyl;
$R^2$ is $(C_1-C_6)$-alkyl,
—CO—$NR^8R^9$,
—$(CH_2)_n$—$NR^8R^9$,
—$(CH_2)_p$—$OR^8$, or
—$(CH_2)_n$—CN;
$R^3$ is selected from hydrogen halogen, halogen-$(C_1-C_6)$-alkyl, cyano, $(C_1-C_6)$-alkoxy or halogen $(C_1-C_6)$-alkoxy;

$R^4$, $R^5$, $R^6$ and $R^7$ are hydrogen or fluoro, wherein at least one of $R^4$, $R^5$, $R_6$ and $R^7$ is fluoro;

$R^8$ and $R^9$ are each independently hydrogen or ($C_1$–$C_6$)-alkyl;

m is 1, 2 or 3;

n is 0, 1, 2 or 3; and p is 1 or 2;

or a pharmaceutically acceptable salt thereof, and a pharmaceutically acceptable carrier.

44. A process for the manufacture of a compound of formula I

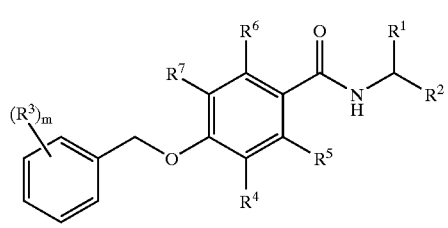

wherein $R^1$ is hydrogen, ($C_1$–$C_6$)-alkyl or hydroxy-($C_1$–$C_6$)-alkyl;

$R^2$ is ($C_1$–$C_6$)-alkyl,
—CO—$NR^8R^9$,
—$(CH_2)_n$—$NR^8R^9$,
—$(CH_2)_p$—$OR^8$, or
—$(CH_2)_n$—CN;

$R^3$ is selected from hydrogen halogen, halogen-($C_1$–$C_6$)-alkyl, cyano, ($C_1$–$C_6$)-alkoxy or halogen-($C_1$–$C_6$)-alkoxy;

$R^4$, $R^5$, $R^6$ and $R^7$ are hydrogen or fluoro, wherein at least one of $R^4$, $R^5$, $R^6$ and $R^7$ is fluoro;

$R^8$ and $R^9$ are each independently hydrogen or ($C_1$–$C_6$)-alkyl;

m is 1, 2 or 3;

n is 0, 1, 2 or 3; and p is 1 or 2;

which process comprises a) reacting a compound of

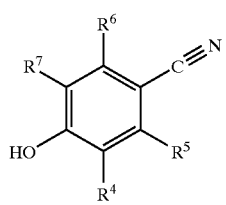

with a compound of formula

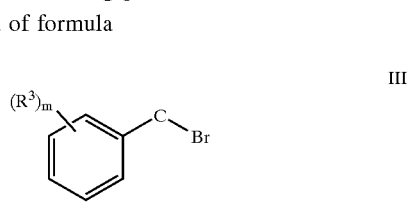

to obtain a compound of formula

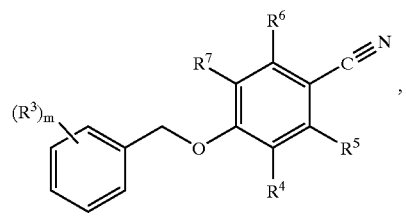

b) transforming compound IV to a compound of formula

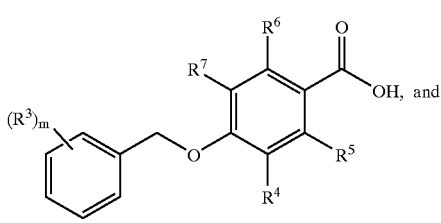

c) treating compound V with compounds of formula

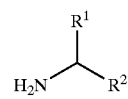

to obtain a compound of formula

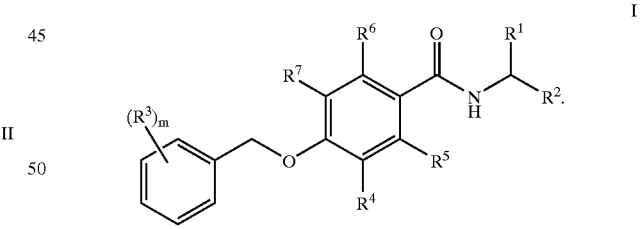

45. The process of claim 44, further comprising converting the compound of formula I to a pharmaceutically acceptable salt.

* * * * *

UNITED STATES PATENT AND TRADEMARK OFFICE
CERTIFICATE OF CORRECTION

PATENT NO. : 6,951,884 B2
APPLICATION NO. : 10/456641
DATED : October 4, 2005
INVENTOR(S) : Jolidon et al.

It is certified that error appears in the above-identified patent and that said Letters Patent is hereby corrected as shown below:

Claim 43, Column 29, line 3: "$R_6$" should read -- $R^6$ --.

Signed and Sealed this

Fourth Day of July, 2006

JON W. DUDAS
*Director of the United States Patent and Trademark Office*